United States Patent
Miyahara et al.

(10) Patent No.: US 6,548,463 B2
(45) Date of Patent: Apr. 15, 2003

(54) CLEANSING AGENTS

(75) Inventors: Reiji Miyahara, Yokohama (JP);
Takashi Ohmori, Yokohama (JP);
Tomiyuki Namba, Yokohama (JP);
Hiroyuki Kakoki, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 09/774,056

(22) Filed: Jan. 31, 2001

(65) Prior Publication Data

US 2001/0021691 A1 Sep. 13, 2001

(30) Foreign Application Priority Data

Jan. 31, 2000 (JP) ........................................ 2000-021556

(51) Int. Cl.[7] ................................................. C11D 1/72
(52) U.S. Cl. ....................................... 510/136; 510/506
(58) Field of Search ................................. 510/136, 506

(56) References Cited

U.S. PATENT DOCUMENTS

| | | | | |
|---|---|---|---|---|
| 4,028,283 A | * | 6/1977 | Murata et al. ............... | 252/551 |
| 4,504,385 A | * | 3/1985 | Keys ........................... | 209/166 |
| 4,549,009 A | * | 10/1985 | Higaki et al. ................ | 528/301 |
| 4,555,442 A | * | 11/1985 | Frentzel ..................... | 428/318.4 |
| 5,437,860 A | | 8/1995 | Jarvis et al. | |
| 5,650,158 A | * | 7/1997 | Eierdanz et al. ............. | 424/401 |
| 5,752,989 A | * | 5/1998 | Henly et al. .................. | 44/347 |

FOREIGN PATENT DOCUMENTS

EP 210642 A2 * 2/1987
EP 813860 A1 12/1997

OTHER PUBLICATIONS

Patent Abstracts of Japan, vol. 004, No. 042 (C–005), Apr. 3, 1980 & JP 55 017310 A Feb. 6, 1980.
Patent Abstracts of Japan, vol. 017, No. 492 (C–1107), Sep. 7, 1993 & JP 05 125396 A, May 21, 1993.
English Translation of Japanese Patent application No. S53–89118, filed Jul. 21, 1978.

* cited by examiner

*Primary Examiner*—John Hardee

(57) ABSTRACT

Cleansing agents are provided which are highly effective for removing makeup with excellent lathering, while at the same time providing a refreshing after-shampoo feeling. These cleansing agents comprise surfactants and polyoxyalkylene carboxylic acid esters represented by the following formula (1):

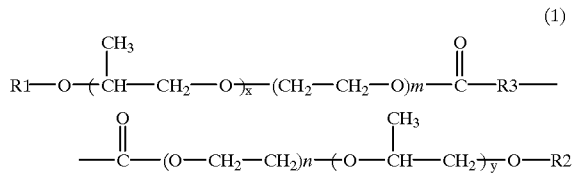

wherein R1 and R2 are hydrogen or straight or branched chain alkyl groups having 1 to 4 carbon atoms; m, n, X and Y are integers of from 0 to 5 but are not all concurrently 0; and R3 is a straight or branched chain alkylene group having from 0 to 10 carbon atoms.

11 Claims, No Drawings

CLEANSING AGENTS

RELATED APPLICATION

This application claims the priority of Japanese Patent application No. 2000-21556 filed on Jan. 31, 2000, which is incorporated herein by reference.

FIELD OF THE INVENTION

The present invention relates in general to cleansing agents and, more particularly, to cleansing agents with excellent lathering which are highly effective for removing makeup.

BACKGROUND OF THE INVENTION

Cosmetic makeup is conventionally removed from the skin by cleansing foams and facial cleansing gels incorporating surfactants as main ingredients, and cleansing oils.

Cleansing foams and facial cleansing gels use the detergency of surfactants to remove makeup cosmetics containing silicone resins. These cleansing agents have the advantage of neatly cleaning in addition to their excellent lathering, but the makeup removal is insufficient.

Although cleansing oils dissolve the coats of makeup cosmetics and are excellent for their cleaning effects, they have had a problem in failing to leave the skin with a refreshing after-wash feeling. Conceptually, these problems could be overcome by combining oils with formulations containing surfactants, since silicone resins contained in makeup cosmetics are soluble in oils. However, in general, oils are insoluble in water, and surfactants are used to solubilize and emulsify these oils. Thus, this approach to solving these problems results in cleansing agents having poor lathering and lacking refreshing feeling.

As a result of extensive studies on these problems, it has been unexpectedly discovered that cleansing agents combining surfactants with certain polyoxyalkylene dicarboxylic acid esters are surprisingly effective for makeup removal with excellent lathering, and can be completely washed out.

SUMMARY OF THE INVENTION

An object of the present invention is to provide cleansing agents which are highly effective for makeup removal with excellent lathering, and which can be neatly and completely washed out.

It has been unexpectedly discovered that these objects can be achieved with cleansing agents comprising surfactants and polyoxyalkylene dicarboxylic acid esters represented by the following formula (1):

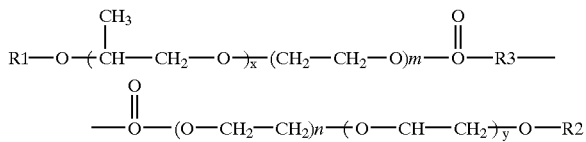

(1)

Wherein R1 and R2 are hydrogen, or straight or branched chain alkyl groups having from 1 to 4 carbon atoms; m, n, X and Y are integers of from 0 to 5 and are not all concurrently 0; and R3 is a straight or branched chain alkylene group having from 0 to 10 carbon atoms.

According to the present invention, the polyoxyalkylene dicarboxylic acid ester is preferably diethoxyethyl succinate.

Additionally, the present invention provides a cleansing agent, wherein the cleansing agent is a makeup remover.

DETAILED DESCRIPTION OF THE INVENTION

The present invention is described in further detail hereinafter.

Polyoxyethylene dicarboxylic acid esters of the above chemical formula (1) used herein is a known compound, but a novel combination of components are used as cleansing agent ingredients according to the present invention.

In the above formula (1), R1 and R2 represent straight or branched chain alkyl groups having from 1 to 4 carbon atoms, but when the number of carbon atoms is 5 or more, the cleansing agent has poor lathering due to lack of hydrophilicity. The symbols m, n, X and Y represent integers of from 0 to 5, preferably of from 1 to 2. When the sum of m, n, X and Y represent 0, the cleansing agent has poor lathering due to lack of hydrophilicity, and when the sum of m, n, X and Y is over 15, the cleansing agent has poor makeup removal due to poor solubility of the makeup cosmetics. R3 represents a straight or branched chain alkylene group of 0 to 10 carbon atoms. When R3 has 11 or more carbon atoms, the cleansing agent has poor lathering due to lack of hydrophilicity.

When the polyoxyalkylene dicarboxylic acid ester of the above formula (1) is diethoxyethyl succinate, the resulting cleansing agent is highly effective for makeup removal with excellent lathering.

The combined amount of polyoxyalkylene dicarboxylic acid ester is not limited in any way, but is preferably from 0.1 to 10% by weight, more preferably from 1 to 10% by weight, and most preferably from 3 to 5% by weight based upon the total weight of the cleansing agent. When the combined amount of the polyoxyalkylene dicarboxylic acid ester of formula (1) is less than 0.1% by weight, the effects of the invention are low and not fully realized, and when the amount is more than 10% by weight, the effects of the invention cannot be exerted due to its separation from water.

The type of surfactant which can be used in the present invention is not limited if the surfactant is generally used in cleansing agents. Suitable examples of surfactants which can be used include fatty acid soaps such as potassium laurate, sodium laurate, triethanol ammonium laurate, potassium myristate, sodium myristate, and triethanol ammonium myristate.

Suitable examples of anion surfactants which can be used include sodium lauryl sulfate, polyoxyethylene alkyl ether sodium sulfate, sodium alkyl β-alanine, sodium sulfosuccinate, acylmethyl taurine, sodium alkylethane sulfonate, and polyoxyethylene alkyl ether sodium carboxylate.

Suitable examples of cation surfactants which can be used include stearyl trimethyl ammonium chloride, benzalkonium chloride, and lauryl amine oxide.

Suitable examples of non ionic surfactants which can be used include sorbitan monolaurate, sorbitan monopalmitate, sorbitan sesquioleate, polyoxyethylene sorbitan monolaurate, polyethylene glycol monooleate, polyoxyethylene alkyl ether, polyglycol diester, lauroyl diethanol amide, fatty acid isopropanol amide, maltitol hydroxy fatty acid alkyl ether, alkylated polysaccharide, alkyl glucoside, and sucrose fatty acid ester.

Suitable examples of ampholytic surfactants which can be used include amide propyl betaine coconut fatty acid, amide propyl betaine laurate, and amide propyl betaine myristate.

The combined amount of surfactants is not limited in any way, and is appropriately determined for each product, but is preferably from 10 to 50% by weight, more preferably from 10 to 40% by weight based upon the total weight of the cleansing agent. In a preferred embodiment, the weight ratio of the polyoxyalkylene dicarboxylic acid ester of formula (1) to the surfactant used in the cleansing agent ranges from about 2 to 100, more preferably from 5 to 80%.

The cleansing agent of the present invention means an agent whose purpose is to cleanse the exodermis of the skin to which can be applied cosmetics, medications and quasi-drugs. In particular, the cleansing agent of the present invention is preferably used for makeup removal such as a cleansing cream which removes makeup cosmetics. The formulations of the present invention can take various forms such as aqueous solutions, emulsions or gels.

In addition to the above-described essential ingredients, the cleansing agents of the present invention can be combined with other ingredients which are normally used in cleansing agents for cosmetics and medications, and the cleansing agents of the present invention can be produced by standard methods.

Other suitable ingredients which can be included in the cleansing agents of the present invention are described, by way of example, below.

Examples of suitable oils which can be included in the formulations of the present invention are avocado oil, macadamia nut oil, corn oil, olive oil, rape oil, evening primrose oil, castor oil, sunflower seed oil, tea seed oil, rice bran oil, jojoba oil, cacao oil, coconut oil, squalene, beef tallow, Japanese wax, bee wax, candelilla wax, Carnauba wax, whale wax, lanolin, liquid paraffin, polyoxyethylene (8 mole) oleyl alcohol ether, and glyceryl monooleate.

Examples of suitable higher alcohols which can be included in the formulation of the present invention are caprylic alcohol, lauryl alcohol, myristate alcohol, cetyl alcohol, cholesterol, and phytosterol.

Examples of suitable higher fatty acids which can be included are capric acid, lauric acid, myristic acid, palmitic acid, stearic acid, behenylic acid, lanolin fatty acid, linoleic acid and linolenic acid.

Examples of suitable humectants which can be included are polyethylene glycol, glycerin, sorbitol, xylitol, maltitol, mucopolysaccharide, hyaluronic acid, chondroitin sulfate, and chitosan.

Examples of suitable thickening agents which can be used are methyl cellulose, ethyl cellulose, gum acacia, and polyvinyl alcohol.

Examples of suitable organic solvents which can be included are ethanol and 1,3-butylene glycol.

Examples of suitable anti-oxidants which can be included are butyl hydroxy toluene, tocopherol, and phytic acid.

Examples of suitable anti-bacterial preservatives which can be included are benzoic acid, salicylic acid, sorbic acid, p-hydroxybenzoate ester (e.g., ethylparaben, butylparaben), and hexachlorophene.

Examples of suitable amino acids and their chlorides which can be included are glycin, alanine, valine, leucine, serine, threonine, phenylalanine, tyrosine, aspartic acid, asparagine, glutamine, taurine, arginine, and histidine.

Examples of suitable organic acids which can be included are acyl sarcosinic acid (e.g., lauroyl sodium sarcosine), glutathione, citric acid, malic acid, tartaric acid, and lactic acid.

Examples of suitable vitamin Bs which can be included are vitamin B6 tripalmitate, vitamin B6 dioctanoate, vitamin B2 and its derivatives, vitamin B12, vitamin B15 and its derivatives. Vitamin Cs are ascorbic acid, ascorbate phosphate ester (salt), and ascorbate dipalmitate.

Examples of suitable vitamin Es which can be included are α-tocopherol, β-tocopherol, γ-tocopherol, vitamin E acetate, and vitamin E nicotinate.

Examples of suitable other vitamins which can be included are vitamin A and its derivatives, vitamin Ds and vitamin H such as pantothenic acid and pantethine.

Examples of various other suitable agents which can be included are nicotinic acid amide, nicotinic acid benzyl, γ-orizanol, allantoin, glycyrrhizinic acid (salts), glycyrrhetinic acid and its derivatives, hinokitiol, mucidin, bisabolol, eucalyptol, thymol, inositol, saponins (psycosaponin, carrot saponin, sponge saponin, sapindaceous saponin), pantothenyl ethyl ether, ethynyl estradiol, tranexamic acid, cepharanthin, placenta extract.

Examples of suitable natural extracts extracted with organic solvents, alcohols, polyhydric alcohols, water and aqueous alcohols which can be included in the cleansing agents of the present invention are sorrel, sophora, nuphar, orange, sage, thyme, milfoil, mallow, cnidium rhizone, swertia herb, Japanese angelicaa root, bitter orange peel, birch, horsetail, sponge gourd, horse chestnut tree, saxifrage, arnica, lily, mugwort, peony root, aloe, gardenia, and Spanish mackerel.

In addition, perfume, scrub agents and purified water and the like can also be included in the cleansing agents of the present invention.

The cleansing agents of the present invention are highly effective for makeup removal with excellent lathering and create a refreshing after-shampoo feeling.

EXAMPLES

Suitable examples of cleansing formulations of the present invention are set forth hereinafter by way of example. However, the formulations of the present invention are not limited to these particular examples described herein. The amounts of the components in the compositions described hereinafter are expressed as % by weight unless otherwise indicated.

Examples 1 to 3, Comparative Example 1

The cleansing gels in the Examples and Comparative examples shown in Table 2 and Table 3 were produced and subjected to detergency tests of lipstick and foaming power tests. As the polyoxyalkylene dicarboxylic acid ester, diethoxyethyl succinate, diethylcarbitol sebacate and ethylethoxyethyl adipate were used. "Detergency tests of lipstick"

The lipstick of which formulation as shown in the following Table 1 was uniformly applied on artificial leather sheets and dried for 10 mins.

TABLE 1

| Formulation of Lipstick | |
|---|---|
| Combined Ingredient | % by Weight |
| 2-Octyl dodecanol | 6.0 |
| Titanium oxide | 1.0 |
| Barium sulfate | 1.0 |
| Mica | 2.0 |
| Vitamin E acetate | 0.1 |

TABLE 1-continued

Formulation of Lipstick

| Combined Ingredient | % by Weight |
|---|---|
| Ion exchanged water | 0.16 |
| Red color = 201 lake pigment | 5.0 |
| Liquid paraffin | 5.0 |
| Solid paraffin | 30.0 |
| Triglyceride caprate/caprylate | 3.0 |
| Propylene glycol dioctanoate | 6.0 |
| 2-Ethylhexyl 12-hydroxystearate | 18.0 |
| 2-Octyldodecyl ricinoleate | 2.0 |
| Ferric oxide | 1.0 |
| Polybutene | 14.74 |

A cotton impregnated with 0.1 g of each sample shown in Examples 1 to 3 and Comparative example 1 was attached on a reciprocating arm, and the cotton piece on the arm weighted with 50 g of load was reciprocated five times on an artificial leather sheet to which lipstick had been applied. Then, the amount of the lipstick on this artificial leather sheet was measured as color differences from colors on unapplied portions using a color-difference meter.

The percentage of the removed lipstick amount for the amount of lipstick before being scrubbed with the sample was calculated to determine the detergency in (%).

The formulations of cleansing gels (test samples) in each Example 1 to 3 and Comparative example 1 are shown in Table 2, and the results are also shown in Table 2.

TABLE 2

Cleansing gels and detergency of lipstick in Examples 1 to 3 and Comparative example 1

| Combined ingredient | Example 1 | Example 2 | Example 3 | Comparative Example 1 |
|---|---|---|---|---|
| Potassium laurate | 5.0 | 5.0 | 5.0 | 5.0 |
| Potassium myristate | 5.0 | 5.0 | 5.0 | 5.0 |
| Amide propylbetaine coconut fatty acid | 5.0 | 5.0 | 5.0 | 5.0 |
| Diethanol amide coconut fatty acid | 3.0 | 3.0 | 3.0 | 3.0 |
| Propylene glycol | 7.0 | 7.0 | 7.0 | 7.0 |
| Glycerin | 5.0 | 5.0 | 5.0 | 5.0 |
| Ion exchanged water | 65.0 | 65.0 | 65.0 | 70.0 |
| Diethoxyethyl succinate | 5.0 | — | — | — |
| Diethylcarbitol sebacate | — | 5.0 | — | — |
| Ethylethoxyethyl adipate | — | — | 5.0 | — |
| Detergency of lipstick | 92 | 87 | 89 | 54 |

As shown in Table 2, the detergency of the lipsticks was found to increase when the polyoxyalkylene dicarboxylic acid ester of the present invention was incorporated in the lipstick. This is especially apparent when the polyoxyalkylene dicarboxylic acid ester was diethoxyethyl succinate when compared with the formulation of Comparative example 1.

Foaming test

The cleansing gels of the present invention were prepared with the formulations set forth in Table 3. Then, each formulation was dissolved in 70 ppm of 1% calcium chloride, and 40 ml each of these solutions was agitated with a mixer for 60 seconds, and the amount of the foam was measured and designated as the foaming power. These formulations are shown in Table 3 together with the results of these tests.

TABLE 3

Cleansing gels and their foaming power in Examples 1 to 3 and Comparative examples 1 to 3

| Combined ingredient | Example 1 | Example 2 | Example 3 | Comparative Example 1 | Comparative Example 2 | Comparative Example 3 |
|---|---|---|---|---|---|---|
| Potassium laurate | 5.0 | 5.0 | 5.0 | 5.0 | 5.0 | 5.0 |
| Potassium myristate | 5.0 | 5.0 | 5.0 | 5.0 | 5.0 | 5.0 |
| Propylbetaine coconut fatty acid amide | 5.0 | 5.0 | 5.0 | 5.0 | 5.0 | 5.0 |
| Diethanol amide coconut fatty acid | 3.0 | 3.0 | 3.0 | 3.0 | 3.0 | 3.0 |
| Propylene glycol | 7.0 | 7.0 | 7.0 | 7.0 | 7.0 | 7.0 |
| Glycerin | 5.0 | 5.0 | 5.0 | 5.0 | 5.0 | 5.0 |
| Ion exchanged water | 65.0 | 65.0 | 65.0 | 70.0 | 65.0 | 65.0 |
| Diethoxyethyl succinate | 5.0 | — | — | — | — | — |
| Diethylcarbitol sebacate | — | 5.0 | — | — | — | — |
| Ethylethoxyethyl adipate | — | — | 5.0 | — | — | — |
| Liquid paraffin | — | — | — | — | 5.0 | — |
| Cetyl isononanoate | — | — | — | — | — | 5.0 |
| Foaming power (mL) | 2050 | 1900 | 1950 | 2000 | 600 | 800 |

As shown in Table 3, the polyoxyalkylene dicarboxylic acid ester was found not to decrease the foaming power of the surfactant as compared with the other oils used, such as liquid paraffin and cethyl isononanoate. Importantly, diethoxyethyl succinate was found to inhibit lathering the least.

As can be seen above, the cleansing agents of the present invention combining polyoxyalkylene dicarboxylic acid esters with surfactants were found to be highly effective for makeup removal with excellent lathering. Other examples of formulations of the present invention are described as follows.

| | Example 4 Cleansing Foam | % by weight |
|---|---|---|
| (1) | Lauric acid | 7.50 |
| (2) | Myristic acid | 2.50 |
| (3) | Stearic acid | 15.00 |
| (4) | Potassium hydroxide | 4.62 |
| (5) | Propylene glycol | 15.00 |
| (6) | Glycerin | 10.00 |
| (7) | Maltitol hydroxy aliphatic (C12, C14) ether | 1.00 |
| (8) | Diethoxyethyl succinate | 1.00 |
| (9) | Perfume | adequately |
| (10) | Purified water | residual |

Process of manufacture

Standard procedures can be used in preparing this formulation. The obtained cleansing foam was highly effective for makeup removal with excellent lathering. Its stability was also found to be good.

| | Example 5 Facial cleansing gel | % by weight |
|---|---|---|
| (1) | Disodium polyoxyethylene sulfosuccinate | 8.0 |
| (2) | Propylbetaine coconut fatty acid amide | 7.0 |
| (3) | Hydroxy lauryl ether sodium acetate | 1.0 |
| (4) | Diethanol amide coconut fatty acid | 2.0 |
| (5) | Citric acid | 1.1 |

-continued

| | Example 5 Facial cleansing gel | % by weight |
|---|---|---|
| (6) | Diethylcarbitol sebacate | 5.0 |
| (7) | Perfume | adequately |
| (3) | Purified water | residual |

Process of Manufacture

Standard procedures can be used to prepare this formulation. The obtained facial cleansing gel was highly effective for makeup removal with excellent lathering. Its stability was also found to be good.

| | Example 6 A transparent soap | % by weight |
|---|---|---|
| (1) | Castor oil | 2.0 |
| (2) | Lauric acid | 6.5 |
| (3) | Myristic acid | 12.0 |
| (4) | Palmitic acid | 3.9 |
| (5) | Stearic acid | 7.6 |
| (6) | Isostearic acid | 2.0 |
| (7) | Sodium hydroxide | 4.0 |
| (8) | Potassium hydroxide | 2.0 |
| (9) | Maltitol | 4.0 |
| (10) | Sorbitol | 10.0 |
| (11) | Glycerin | 11.0 |
| (12) | EDTA-3Na-2H$_2$O | 0.05 |
| (13) | Ethanol | 10.00 |
| (14) | Diethyl olyoxyethylenyl succinate (3 mol) | 2.0 |
| (15) | Perfume | adequately |
| (16) | Purified water | residual |

Process of manufacture

Standard procedures can be used in preparing this formulation. The obtained transparent soap was highly effective for makeup removal with excellent lathering. Its stability was also found to be good.

| | Example 7 Liquid facial cleansing agent | % by weight |
|---|---|---|
| (1) | Potassium laurate | 5.0 |
| (2) | Potassium myristate | 5.0 |
| (3) | Propylbetaine coconut fatty acid amide | 5.0 |
| (4) | Diethanol amide coconut fatty acid | 3.0 |
| (5) | Hydroxy lauryl ether sodium acetate | 4.0 |
| (6) | Maltitol hydroxyalkyl (C12, C14) ether | 2.0 |
| (7) | 1,3-butanediol | 10.0 |
| (8) | Glycerin | 5.0 |
| (9) | Diethoxyethyl succinate | 5.0 |
| (10) | Perfume | adequately |
| (11) | Purified water | residual |

Process of manufacture

Standard procedures can be used to prepare this formulation. The obtained liquid facial cleansing agent was highly effective for makeup removal with excellent lathering. Its stability was also found to be good.

| | Example 8 Cleansing gel | % by weight |
|---|---|---|
| (1) | Methyl alanine sodium coconut oil fatty acid | 50.0 |
| (2) | Propylbetaine laurate amide | 35.0 |
| (3) | Monoethanol amide coconut oil fatty acid | 3.0 |
| (4) | Citric acid | 1.0 |
| (5) | Ethylethoxyethyl adipate | 0.5 |
| (6) | Perfume | adequately |
| (7) | Purified water | residual |

Process of Manufacture

Standard procedures can be used for preparing this formulation. The obtained cleansing gel was highly effective for makeup removal with excellent lathering. Its stability was also found to be good.

The cleansing agents for hair in Examples and Comparative examples were also evaluated by the following tests:

Evaluation (1): smoothness of hair after washing

A practical use test was carried out by ten special panelists to examine hair smoothness after washing. The evaluation criterion are as follows:

++; Eight or more special panelists have agreed with hair smoothness after washing.

+; Six or more to less than eight special panelists have agreed with hair smoothness after washing.

±; three or more to less than six special panelists have agreed with hair smoothness after washing.

−; Less than three special panelists have agreed with hair smoothness after washing.

Evaluation (2): smoothness of hair after shampoo and drying

A practical use test was carried out by ten special panelists to examine hair smoothness after shampoo and drying, and hair smoothness after natural drying and that before shampoo were sensually evaluated by a comparative method. The evaluation criterion are as follows:

++; Eight or more special panelists have agreed with more smoothness after shampoo.

+; Six or more to less than eight special panelists have agreed with more smoothness after shampoo.

±; Three or more to less than six special panelists have agreed with more smoothness after shampoo.

−; Less than three special panelists have agreed with more smoothness after shampoo.

Evaluation (3): evaluation of sticky feeling of hair after shampoo and drying

The practical use tests were carried out by ten special panelists to ascertain any sticky feeling of hair after shampoo and drying. Any sticky feeling of hair after natural drying, and those before shampoo were sensually evaluated by a comparative method. The evaluation criterion are as follows:

++; None of the special panelists discerned any sticky feeling.

+; One or more to less than three special panelists have agreed there was more sticky hair after shampoo.

±; Three or more to less than five special panelists have agreed there was more sticky hair after shampoo.

±; Five or more of special panelists have agreed there was more sticky hair after shampoo.

Evaluation (4)—Foaming power test

The formulations in Tables 4 and 5, each at 3%, was dissolved in 70 ppm of calcium chloride solution, and 400 ml of each mixture was then agitated with a mixer for 60 seconds. The amount of foam was measured and determined as the foaming power.

The evaluation criterion was as follows:

++; 2400 ml or more
+; 2000 ml or more to less than 2400 ml
±; 1500 ml or more to less than 2000 ml
−; less than 1500 ml Examples 1 to 6, Comparative Examples 1 to 4

The cleansing agents for hair comprising combined compositions described in Tables 4 and 5. Examples 1 to 6 and Comparative examples 1 to 4 were manufactured by standard procedures, the evaluation tests for hair were carried out for the above evaluation (1), (2), (3) and (4), and the results of these tests are shown in the following Tables 4 and 5 below:

TABLE 4

| | Example | | | | | |
|---|---|---|---|---|---|---|
| Combined ingredient | 1 | 2 | 3 | 4 | 5 | 6 |
| Sodium cocoyl methyl taurine | 20 | 20 | 20 | 20 | 20 | 20 |
| Diethanol amide coconut fatty acid | 3 | 3 | 3 | 3 | 3 | 3 |
| Sodium benzoate | 0.5 | 0.5 | 0.5 | 0.5 | 0.5 | 0.5 |
| Diethoxyethyl succinate | 0.001 | 0.01 | 0.1 | 1.0 | 5.0 | 15.0 |
| Coloring materials | adq | adq | adq | adq | adq | adq |
| Perfumes | adq | adq | adq | adq | adq | adq |
| Purified water | res | res | res | res | res | res |
| Ev(1) Smoothness in washing hairs | + | + | ++ | ++ | ++ | ++ |
| Ev(2) Smoothness after shampoo | + | + | ++ | ++ | ++ | ++ |
| Ev(3) Sticky feeling after shampoo | ++ | ++ | ++ | ++ | ++ | + |
| Ev(4) Foaming power | ++ | ++ | ++ | ++ | ++ | + | adq, adequately;
res, residual;
Ev, Evaluation

TABLE 5

| | Comparative example | | | |
|---|---|---|---|---|
| Combined ingredient | 1 | 2 | 3 | 4 |
| Sodium cocoyl methyl taurine | 20 | — | 20 | — |
| Polyoxyethylene (EO average 3 moles) sodium lauryl ether sulfate | — | 20 | — | 20 |
| Diethanol amide coconut fatty acid | 3 | 3 | 3 | 3 |
| Sodium benzoate | 0.5 | 0.5 | 0.5 | 0.5 |
| Diethoxyethyl succinate | — | — | — | — |
| Pentaerythrityl tetraoctanoate | — | — | 5.0 | 5.0 |
| Color materials | adq | adq | adq | adq |
| Perfumes | adq | adq | adq | adq |
| Purified water | res | res | res | res |
| Evaluation (1) smoothness in washing hairs | − | − | ± | ± |
| Evaluation (2) smoothness after shampoo | − | − | ± | ± |
| Evaluation (3) sticky feeling after shampoo | + | + | − | − |
| Evaluation (4) Foaming power | ++ | ++ | − | − | adq, adequately;
res, residual

As can be seen in Tables 4 and 5, the cleansing agents for hair used in the Examples of the present invention are superior in hair feelings, especially smoothness in washing and after shampoo and have excellent lather as compared with those used in the comparative examples.

What is claimed is:

1. A cleansing agent comprising one or more surfactants and one or more polyoxyalkylene dicarboxylic acid esters represented by the following formula (1):

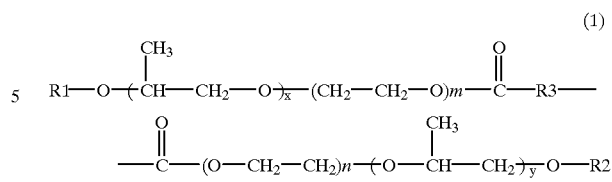

wherein R1 and R2 are hydrogen, or straight or branched chain alkyl groups having from 1 to 4 carbon atoms; m, n, X and Y are integers of from 0 to 5 and are not all concurrently 0; and R3 is a straight or branched chain alkylene group having from 0 to 10 carbon atoms.

2. The cleansing agent of claim 1, wherein said polyoxyalkylene dicarboxylic acid ester is diethoxyethyl succinate.

3. The cleansing agent according to claim 2, wherein said cleansing agent is a makeup remover.

4. The cleansing agent according to claim 1, wherein said cleansing agent is a makeup remover.

5. A cleansing agent comprising at least one surfactant and at least one polyoxyalkylene dicarboxylic acid ester represented by the following formula (1):

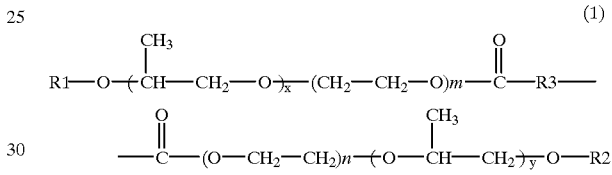

wherein R1 and R2 are hydrogen, or straight or branched chain alkyl groups having from 1 to 4 carbon atoms; m, n, X and Y are integers of from 0 to 5 and are not all concurrently 0 and the sum of m, n, X and Y is 15 or less; and R3 is a straight or branched chain alkylene group having from 0 to 10 carbon atoms, and the polyoxyalkylene diacarboxylic acid ester constitutes from 0.1 to 10% by weight of the total weight of the cleansing agent.

6. The cleansing agent of claim 5, wherein said polyoxyalkylene dicarboxylic acid ester is diethoxyethyl succinate.

7. The cleansing agent according to claim 6, wherein said cleansing agent is a makeup remover.

8. The cleansing agent according to claim 5, wherein said cleansing agent is a makeup remover.

9. A cleansing agent comprising one or more surfactants and one or more polyoxyalkylene dicarboxylic acid esters represented by the following formula (1):

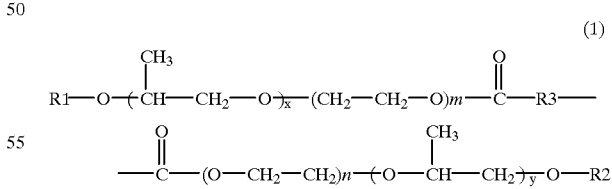

wherein R1 and R2 are hydrogen, or straight or branched chain alkyl groups having from 1 to 4 carbon atoms; m, n, X and Y are integers of from 1 to 2, and the sum of m, n, X and Y is 15 or less; and R3 is a straight or branched chain alkylene group having 0 to 10 carbon atoms, and the polyoxyalkylene dicarboxylic acid ester constitutes from 1.0 to 10% by weight of the total weight of the cleansing agent and the surfactants constitute from 10 to 50% by weight based on the total weight of the cleansing agent.

10. The cleansing agent of claim 9, wherein the surfactant is selected from the group consisting of fatty acid soaps, anion surfactants, cation surfactants, and non-ionic surfactants.

11. The cleansing agent according to claim 1, wherein said cleansing agent is a makeup remover.

* * * * *